(12) United States Patent
Snow et al.

(10) Patent No.: US 11,612,507 B2
(45) Date of Patent: Mar. 28, 2023

(54) ADJUSTABLE LOW-PROFILE ORTHOPEDIC HIP BRACE

(71) Applicant: Arctic Bracing, LLC, McKinney, TX (US)

(72) Inventors: Brian Snow, Fairview, TX (US); Jeff King, Melissa, TX (US)

(73) Assignee: Arctic Bracing, LLC, McKinney, TX (US)

( * ) Notice: Subject to any disclaimer, the term of this patent is extended or adjusted under 35 U.S.C. 154(b) by 752 days.

(21) Appl. No.: 16/557,291

(22) Filed: Aug. 30, 2019

(65) Prior Publication Data

US 2020/0069452 A1 Mar. 5, 2020

Related U.S. Application Data

(60) Provisional application No. 62/725,456, filed on Aug. 31, 2018.

(51) Int. Cl.
| | | |
|---|---|---|
| A61F 5/00 | (2006.01) | |
| A61F 5/01 | (2006.01) | |
| A61F 7/00 | (2006.01) | |
| A61F 7/10 | (2006.01) | |

(52) U.S. Cl.
CPC .......... *A61F 5/0193* (2013.01); *A61F 7/0085* (2013.01); *A61F 7/10* (2013.01); *A61F 2007/0056* (2013.01); *A61F 2007/108* (2013.01)

(58) Field of Classification Search
USPC ....................................... 602/24, 16
See application file for complete search history.

(56) References Cited

U.S. PATENT DOCUMENTS

| | | | |
|---|---|---|---|
| 2012/0259259 A1* | 10/2012 | Chugunov | A61F 5/0123 602/26 |
| 2014/0188022 A1* | 7/2014 | Hennessy | A61F 5/0102 602/16 |
| 2014/0228726 A1* | 8/2014 | Kruijsen | A61F 5/0193 602/16 |
| 2014/0276311 A1* | 9/2014 | Hollister | A61F 5/0193 602/24 |
| 2015/0374532 A1* | 12/2015 | Fedon | A61F 5/0102 602/16 |
| 2018/0098873 A1* | 4/2018 | Kramer | A61B 5/48 |
| 2018/0161188 A1* | 6/2018 | Zistatsis | A61H 1/024 |
| 2018/0243156 A1* | 8/2018 | Tryba | A61H 3/02 |
| 2018/0280178 A1* | 10/2018 | Shimada | B25J 9/1045 |

* cited by examiner

*Primary Examiner* — Kim M Lewis
(74) *Attorney, Agent, or Firm* — Alliance IP, LLC

(57) ABSTRACT

A hip brace is provided which includes an iliac crest pressure plate, a femur pressure plate, a quadriceps pressure plate, and a bracket to connect the plates. The bracket includes one or more adjustable hinges to adjust positioning of at least one of the iliac crest pressure plate, the femur pressure plate, or the quadriceps pressure plate to correspond with dimensions of a user. The bracket further includes a range of motion restriction dial to control flexion or extension of the hip of the user, where the range of motion restriction is positioned on the bracket to correspond to the femur pressure plate.

26 Claims, 15 Drawing Sheets

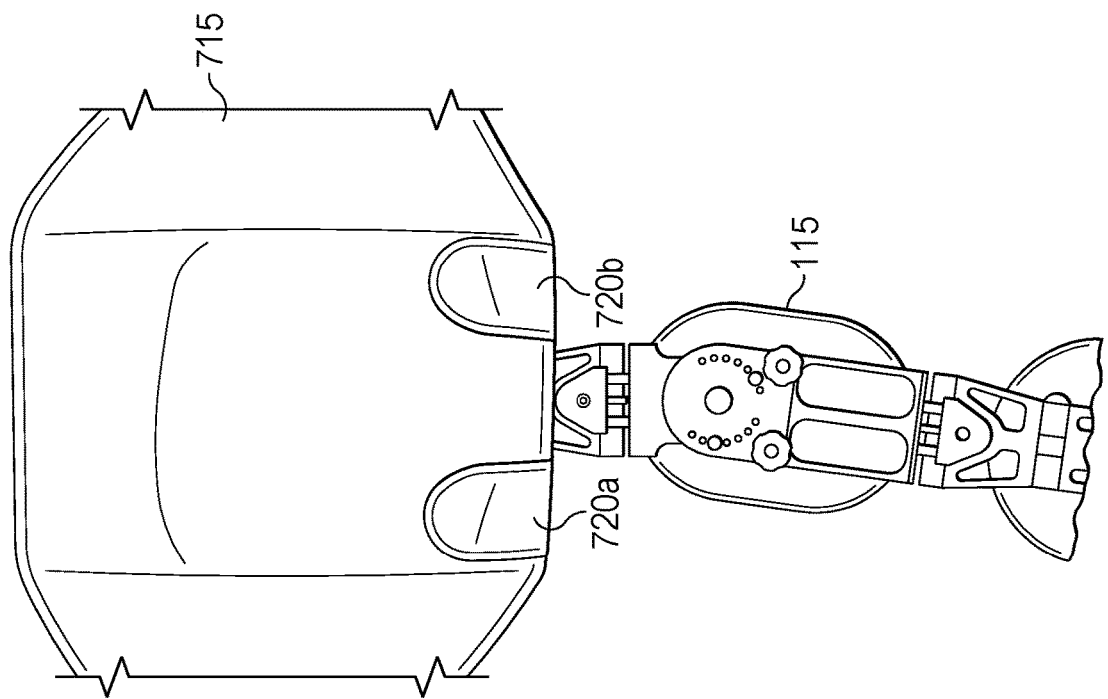
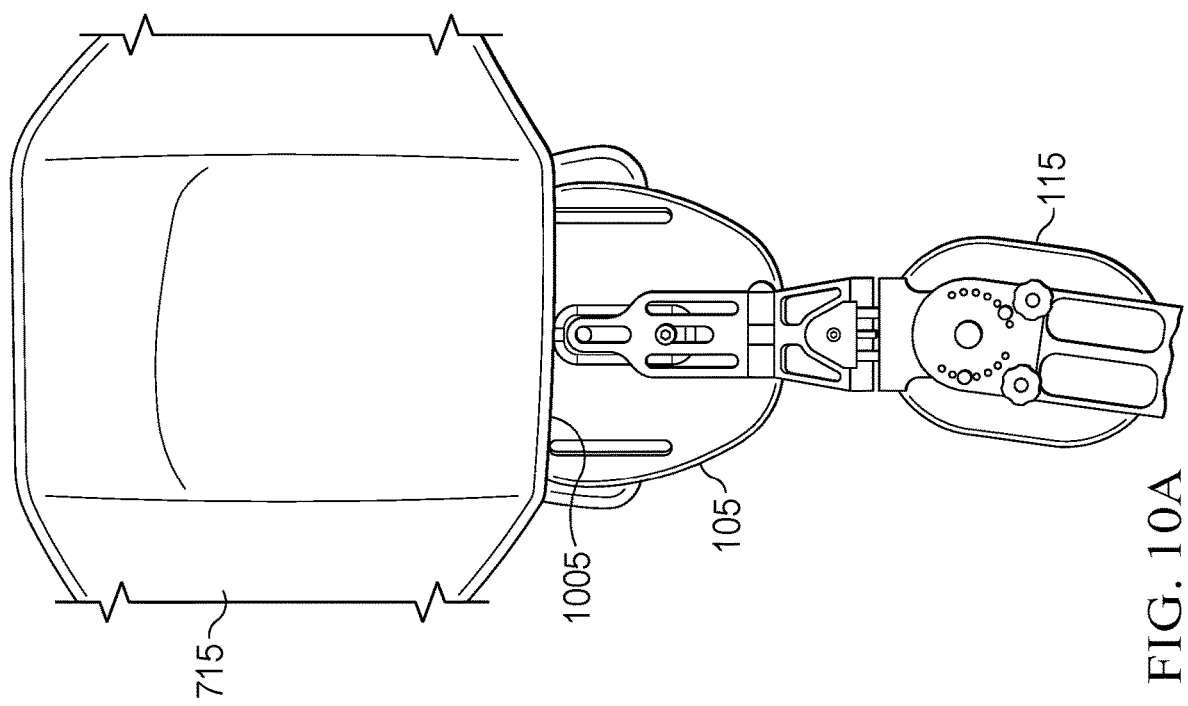

ADJUSTABLE LOW-PROFILE ORTHOPEDIC HIP BRACE

This application claims benefit to U.S. Provisional Patent Application Ser. No. 62/725,456, filed Aug. 31, 2018, the disclosure of which is incorporated by reference herein in its entirety.

BACKGROUND

The present disclosure relates in general to the field of orthopedic devices, and more specifically, to a low-profile, adjustable hip brace.

Orthoses, or orthopedic devices, serve as medical aids for stabilizing, relieving stress, immobilization and, in particular, for guiding or correcting a patient's limbs and joints, including the corresponding muscle tissue, ligaments, and bone structures. Generally, mechanical stabilization and guiding or correction is achieved in particular by mechanically rigid stabilizing elements in the orthopedic devices, which are brought into firm mechanical contact with the body such that supporting forces can be absorbed or correction forces can be exerted. Mechanical joint rails and bridges are often employed, in connection with rigid frames or other structure to provide such protection, correction, and guidance. A range of orthopedic devices have been developed for various parts of the human body (as well as for veterinary uses), including braces for knees, hips, spine, elbow, wrists, ankles, etc.

BRIEF DESCRIPTION OF THE DRAWINGS

FIGS. 10A-10B illustrate insertion of a pressure plate of a hip brace within a pocket of a belt apparatus for use in securing the hip brace to a user in accordance with at least some embodiments.

Like reference numbers and designations in the various drawings indicate like elements.

DETAILED DESCRIPTION OF EXAMPLE EMBODIMENTS

In the following description, numerous specific details are set forth regarding the device and methods of the disclosed subject matter and the environment in which such systems and methods may be deployed or used, etc., in order to provide a thorough understanding of the disclosed subject matter. It will be apparent to one skilled in the art, however, that the disclosed subject matter may be practiced without such specific details, and that certain features, which are well known in the art, are not described in detail in order to avoid complication of the disclosed subject matter. In addition, it will be understood that the embodiments provided below are exemplary, and that it is contemplated that there are other systems and methods that are within the scope of the disclosed subject matter.

Traditional hip braces used by patients and offered by physicians and physical therapists are considered by many, and in particular the brace wearers, to be heavy and bulky. For instance, traditional hip braces are known to weigh 3 pounds or more and can protrude from the wearer in a manner which impedes their maneuverability and comfort. Accordingly, traditional hip braces have a reputation for being cumbersome, difficult to apply and are further deficient in their limited customizability and applicability to different shaped and sized patients.

Example Implementations of improved hip braces are described herein, which resolve and improve upon at least some of the example issues identified above. For instance, an improved hip brace can improve upon customization to a user and comfort, which thereby directly impact what may be considered the most important factor of bracing, namely, patient compliancy—a patient's motivation to faithfully utilize the brace in accordance with an associated treatment plan. In some implementations, an improved hip brace can be fit and quickly customized to most patients (e.g., in under 5 minutes). For instance, in some embodiments, an improved, multi-point customization (e.g., 7 point) may be provided on the hip brace to achieve the most accurate patient fit outside of expensive, made-to-order, custom fabricated braces. After patient customization, a patient can apply the brace with no assistance in a matter of minutes, with this ease of use drastically increasing patient compliancy. In some implementations, the improved hip brace may also facilitate the application of cold therapy treatments, in addition to the traditional function of bracing, to give patients a simple solution to applying recirculating cold pads while providing a necessary barrier to the skin, among other example features and advantages.

Figure 1:
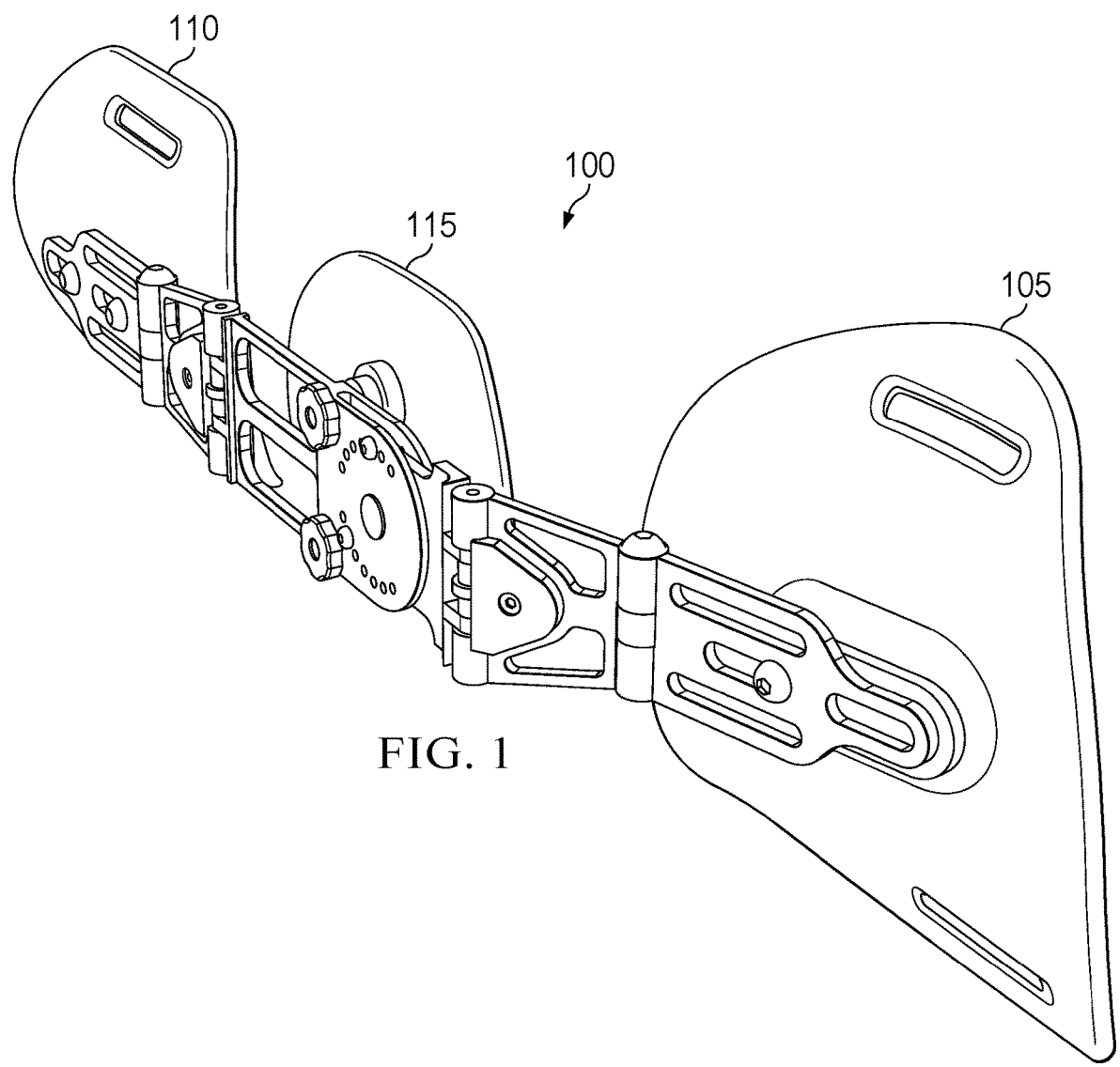
FIG. 1 is a perspective view of an example adjustable, low-profile hip brace in accordance with at least some embodiments.

FIG. 1 is a perspective view of an example implementation of an adjustable, low-profile hip brace device 100. The hip brace device 100 may include three plates to come into contact with the user's body (e.g., either directly or through a padded or ice therapy surface). For instance, the hip brace device 100 may include, at its upper end, an iliac crest pressure plate 105 to correspond with and come in contact with the portion of the user's hip at or near the iliac crest of the user's pelvis. Additionally, a quadricep pressure plate 110 may be provided at the other (lower) end of the brace device 100 and come in contact with the thigh above the knee of the user (and at least the lower portion of the user's quadricep). Additionally, a third femur plate 115 may be provided between the iliac crest pressure plate 105 and quadricep pressure plate 110 to contact and apply pressure at the side of the user's upper thigh below the user's hip (e.g., near the femur). Adjustment mechanisms may be provided on and/or between the plates 105, 110, 115 to facilitate multipoint adjustment and customization of the hip brace device 100 to a variety of different users with a variety of different body shapes.

Figure 2:
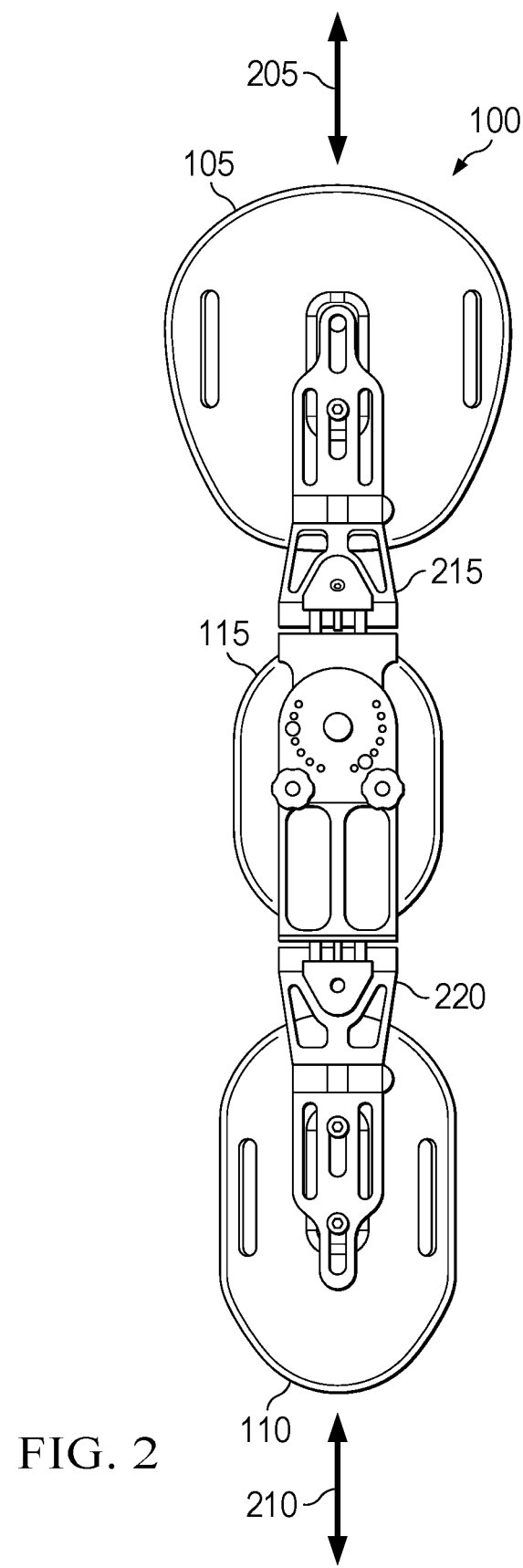
FIG. 2 is a front view of an example adjustable, low-profile hip brace in accordance with at least some embodiments.

For instance, as illustrated in the front view of the hip brace device 100, shown in FIG. 2, mechanisms may be provided to enable upward or downward adjustment (e.g., 205, 210) of the placement of the iliac crest pressure plate 105 and quadricep pressure plate 110. For instance, in one implementation, a bracket may be provided to interconnect the iliac crest pressure plate 105, quadricep pressure plate 110, and femur pressure plate 115 of the hip brace device 100. Indeed, respective bracket segments (e.g., 215, 220) may be provided to connect each of the iliac crest pressure plate 105 and the quadricep pressure plate 110 to the femur pressure plate 115. In one example, sliding lock bolts may be provided on one or both of the iliac crest pressure plate 105 and/or quadricep pressure plate 110 to enable the corresponding plate (e.g., 105, 110) to slide within an opening provided on the bracket segment (e.g., 215, 220) to reposition each plate (e.g., 105, 110) on the bracket segment (e.g., 215, 220), as shown at 205, 210. Such adjustments may allow each of the iliac crest pressure plate 105 and the quadricep pressure plate 110 to be repositioned in a roughly vertical plan relative to the position of the femur pressure plate 115, thereby allowing each of the plates to be positioned along a user's hip and leg to correspond with the user's specific body (e.g., to correspond with the specific positions of the user's iliac crest, upper femur shaft, and lower portion of the quadricep (e.g., at or near the user's vastus lateralis)). The overall length of the hip brace may also be thereby elongated or shortened in accordance with the height/length adjustments made based on the specific dimensions of the patient/user.

Figure 3:
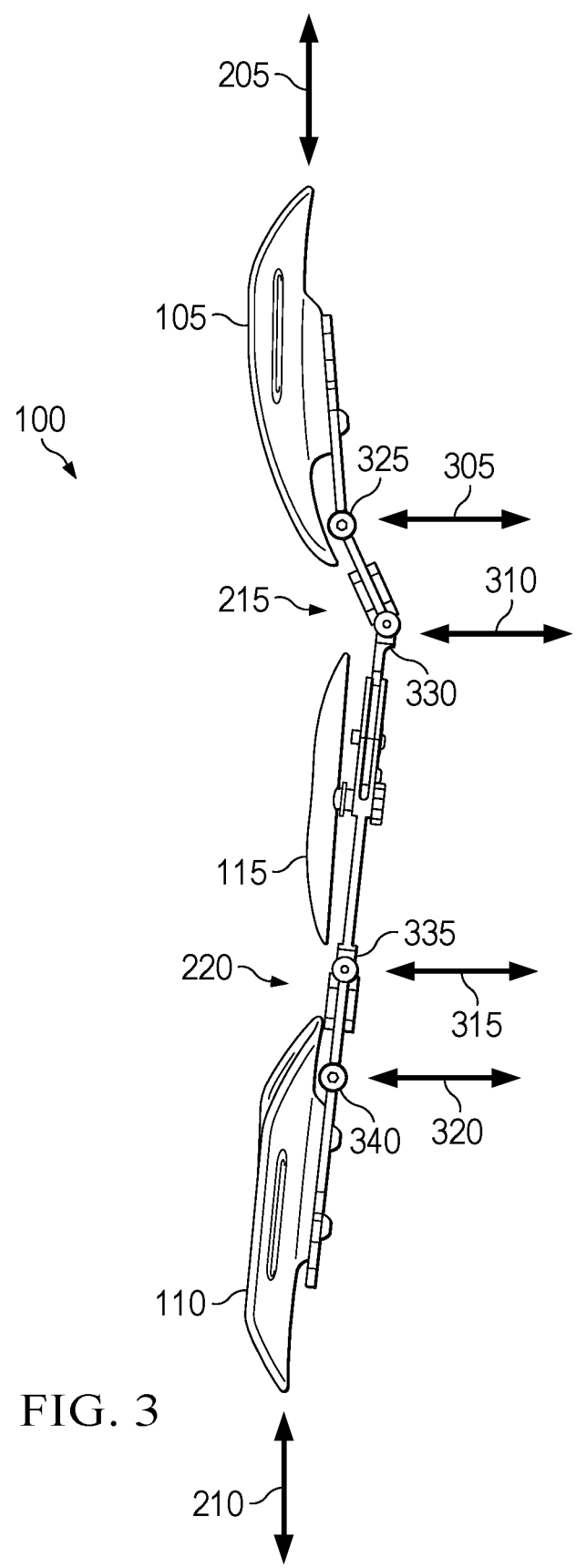
FIG. 3 is a side view of an example adjustable, low-profile hip brace in accordance with at least some embodiments.

As introduced above, an improved, low-profile hip brace device 100 may enable multi-point adjustment and customization, with further adjustments being enabled in accordance with the side view of an example hip brace device 100 shown in FIG. 3. For instance, the brackets segments (e.g., 215, 220) forming the bracket of the hip brace may include adjustable and locking hinges (e.g., 325, 330 and 335, 340 respectively) to enable the positions of of each of the iliac crest pressure plate 105 and the quadricep pressure plate 110 to be further adjusted. For instance, hinges 325 and 340 may be used to adjust the respective angle of the iliac crest pressure plate 105 and the quadricep pressure plate 110 to be conform to the specific contours of the patient's body. For instance, adjusting the hinges 325, 340 inward and outward (e.g., 305, 320) allows the angles of both the iliac crest pressure plate 105 and the quadricep pressure plate 110 to be adjusted relative to the femur plate 115. In some implementations, a locking hinge 325 for the iliac crest plate 105 may be provided just below the sliding bolt opening on the bracket segment 215 to correspond to the iliac crest pressure plate 105 and another locking hinge 335 just above the sliding bolt opening on the bracket segment 220 to correspond to the quadricep pressure plate 110. These hinges 325, 335 may be respectively unlocked to manipulate the positions of each of the iliac crest pressure plate 105 and quadricep pressure plate 110 and when the proper dimensions are determined for the particular patient, these lock hinges may be relocked to provide a laterally rigid brace fit to the contours (e.g., waist and thigh size) of the patient. Further, these adjustable locking hinges may be easily adjusted (e.g., by a medical care technician or by the user themselves) to adjust the same hip brace to another, different user or to accommodate for weight loss/gain in the same user to account for changes in the user's physique, among other examples.

Additionally, as further illustrated in FIG. 3, an improved low-profile hip brace may be equipped with additional hinges or joints (e.g., 330, 335) to enable the hip brace 100 to be further adjusted to respectively move each of the iliac crest pressure plate 105 and the quadricep pressure plate 110 inward or outward (e.g., 310, 315) relative to the femur pressure plate 115 to thereby move the femur pressure plate 115 toward or away from the patient/user's body and further customize the fit of the hip brace 100 to the user. These customizations collectively improve both the correction functions of the brace device 100 as well as the comfort to the user. For instance, one or both of hinges 330, 335 may be implemented using worm gear hinges positioned to correspond to the top and bottom of the femur pressure plate 115. These adjustable hinges 330, 335 may also be manipulated (e.g., at 310, 315) to cause either or both the top (nearest the iliac crest pressure plate 105) and bottom (nearest the quadricep pressure plate 110) ends of the femur plate 115 to be repositioned inward toward the femur of the wearer, or outward, so at provide the sufficient amount of pressure to fit the hip brace device 100 to the specific leg size and dimensions of the wearer.

Figure 4:
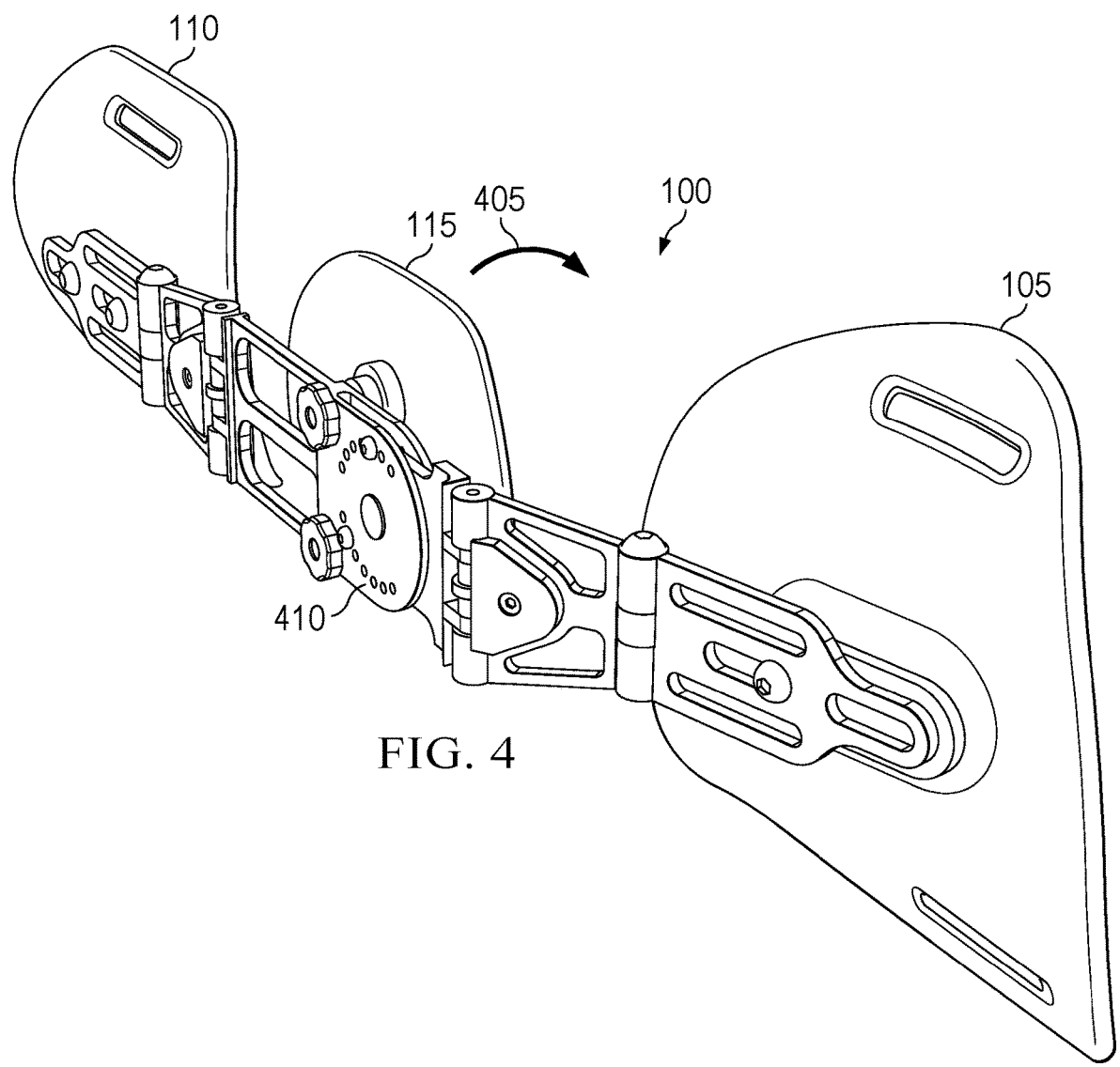
FIG. 4 is a perspective view of an example adjustable, low-profile hip brace with an adjustable femur pressure plate in accordance with at least some embodiments.

Turning to the perspective view of the example hip brace device 100 shown in FIG. 4, additional mechanisms may be provided on the brace device 100 to enable the femur pressure plate 115 to be rotated (e.g., about an axis running the length of the brace from approximately the top of the iliac crest plate 105 to the bottom of the quadricep plate 110) to cause the femur pressure plate 115 to be biased (e.g., 405) biased either toward the posterior or anterior side of the wearer's leg. For instance, turning an anterior/posterior pad adjustment dial may be provided at or near the femur pressure plate or on the bracket (e.g., at bracket segment 215 or 220) connected to the femur pressure plate 115 to can cause slight rotation (e.g., 405) along the axis of the hinge on the side corresponding to the adjusted dial. For instance, both an anterior pad adjustment dial and a posterior pad adjustment dial may be provided on the hip brace device 100, where turning one dial more than the other causes one side of the hinge to be biased more than the other (and create an anterior or posterior bias of the femur pressure plate 115). The dials may also be turned to further move the femur pressure plate inward or outward from the femur of the wearer, among other example adjustments.

Indeed, the collective multi-point adjustment mechanisms provided on the example hip brace device 100 represented in FIGS. 2-4 provides seven points of customization to custom fit the hip brace (e.g., through the help and expertise of an attending physician or other medical professional) to a variety of different patients of potentially varying sizes. For instance sliding lock bolts on the iliac crest pressure plate 105 and quadricep pressure plate 110 (as illustrated in FIG. 2) enables the length of hip brace and the distance between each of the plates 105, 110 and the center femur pressure plate 115 to be adjusted and correctly fit the same hip brace device to a variety of different sized patients (e.g., patients with heights ranging from 4'6" up to 6'8"). Further, hinges may be provided on the bracket (as shown in the example of FIG. 3) to respectively make quick adjustments to the angles of each of the iliac crest pressure plate 105 and quadricep pressure plate 110 and enable the same hip brace to accommodate potentially any circumference waist and/or quadricep. Additional adjustable hinges may be provided to cause the femur pressure plate 115 to telescope toward or away from the patient's leg. Adjustment of the femur pressure plate 115 through such mechanisms applies counterpressure (vis-a-vis the pressure applied through the iliac crest pressure plate 105 and quadricep pressure plate 110) to displace the force along the thigh preventing adduction or abduction. Pressure can thereby be adjusted pending soft tissue mass and circumference of the specific thigh of the user. Further, anterior and posterior pressure pad dial adjustments at or near the femur pressure plate may enable the front and back of the femur pressure pad to be manipulated to apply a complete fit to the patient, thereby displacing pressure and creating a secure leverage point.

Figure 5A:
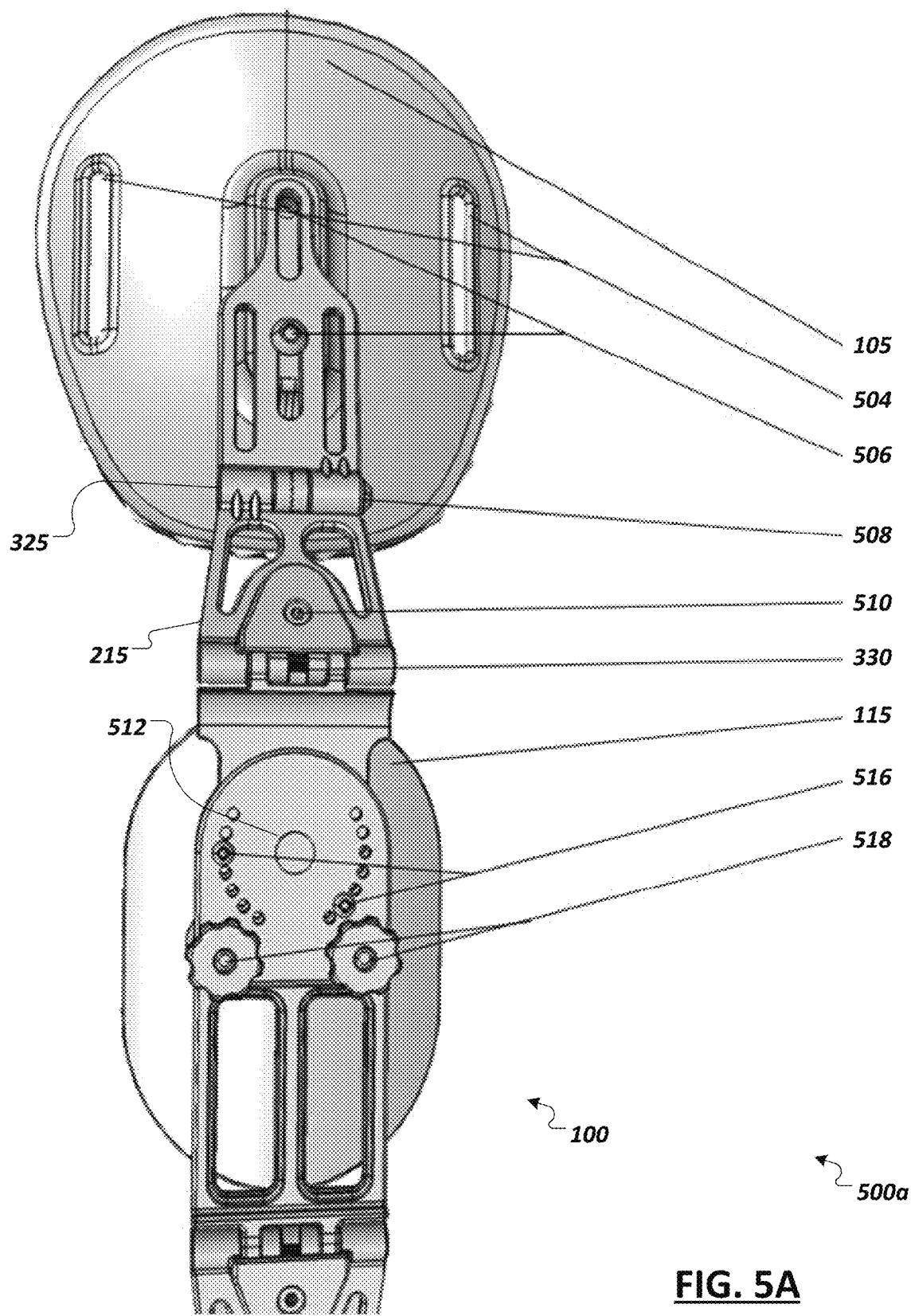
FIGS. 5A-5B are partial front views of an example adjustable, low-profile hip brace in accordance with at least some embodiments.
Figure 5B:
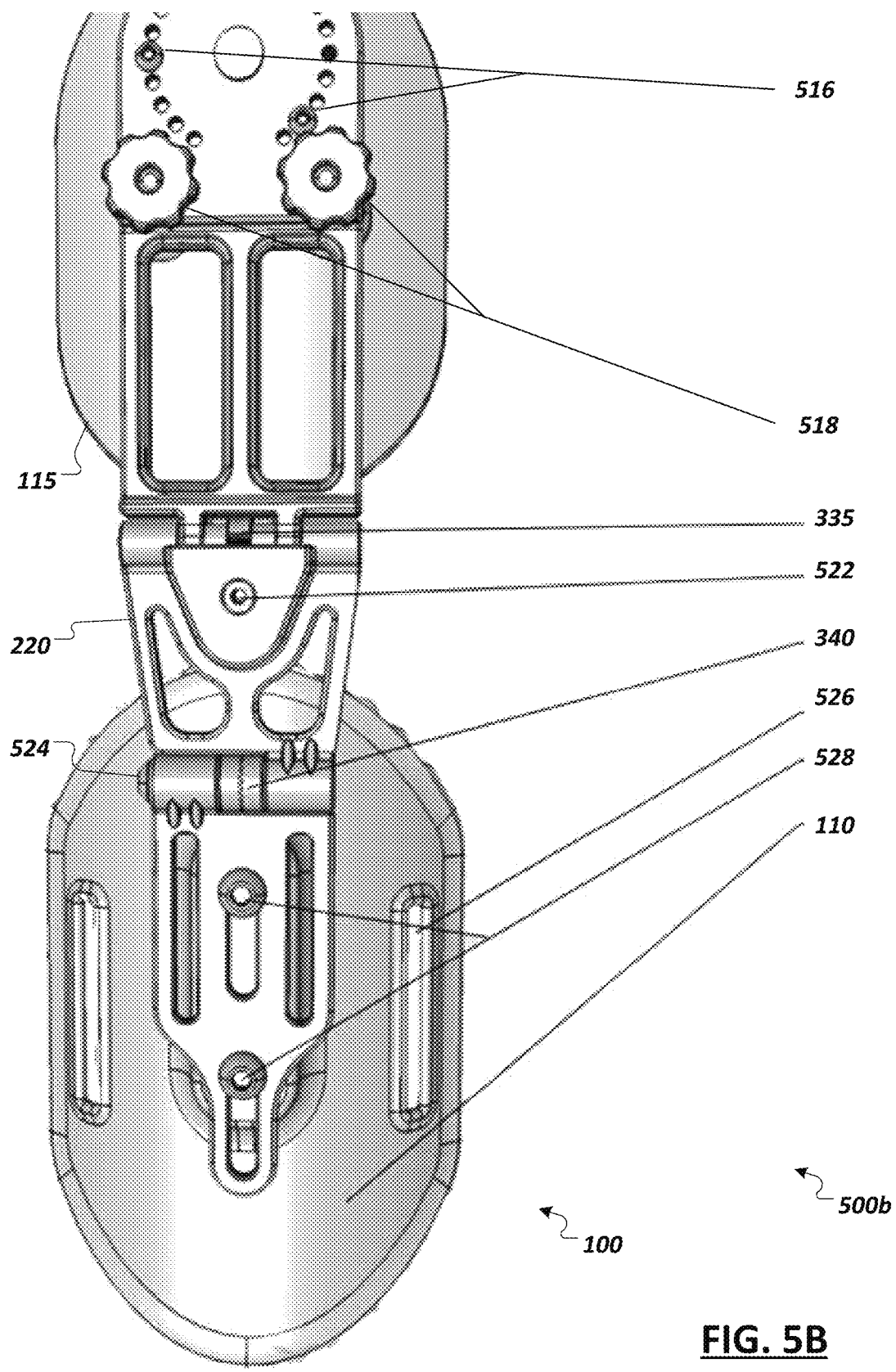
Figure 5C:
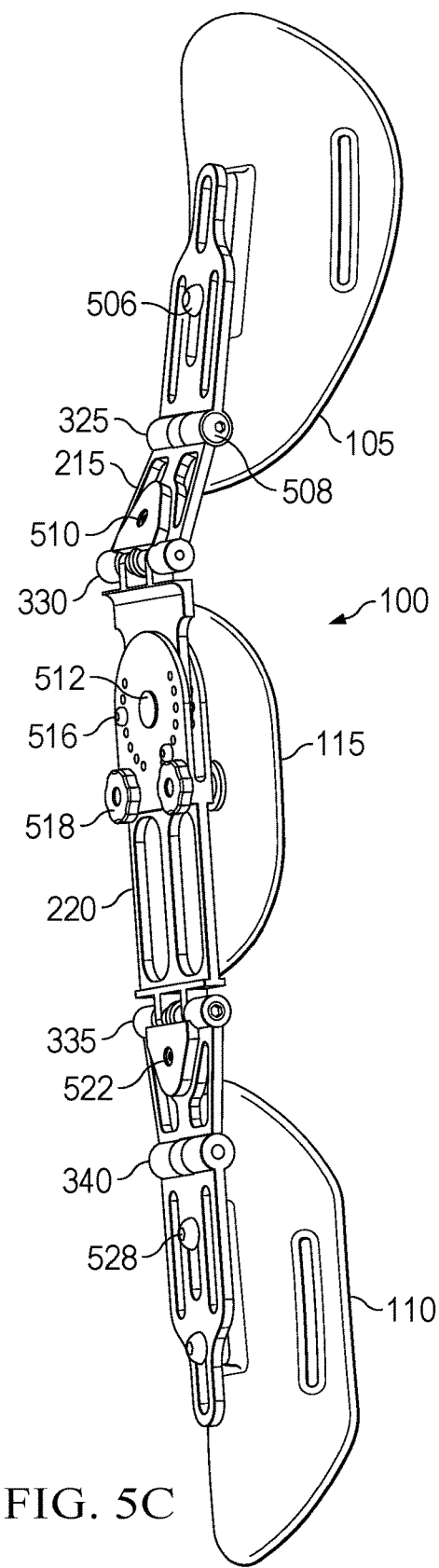
FIGS. 5C-5D are partial side views of an example adjustable, low-profile hip brace in accordance with at least some embodiments.
Figure 5D:
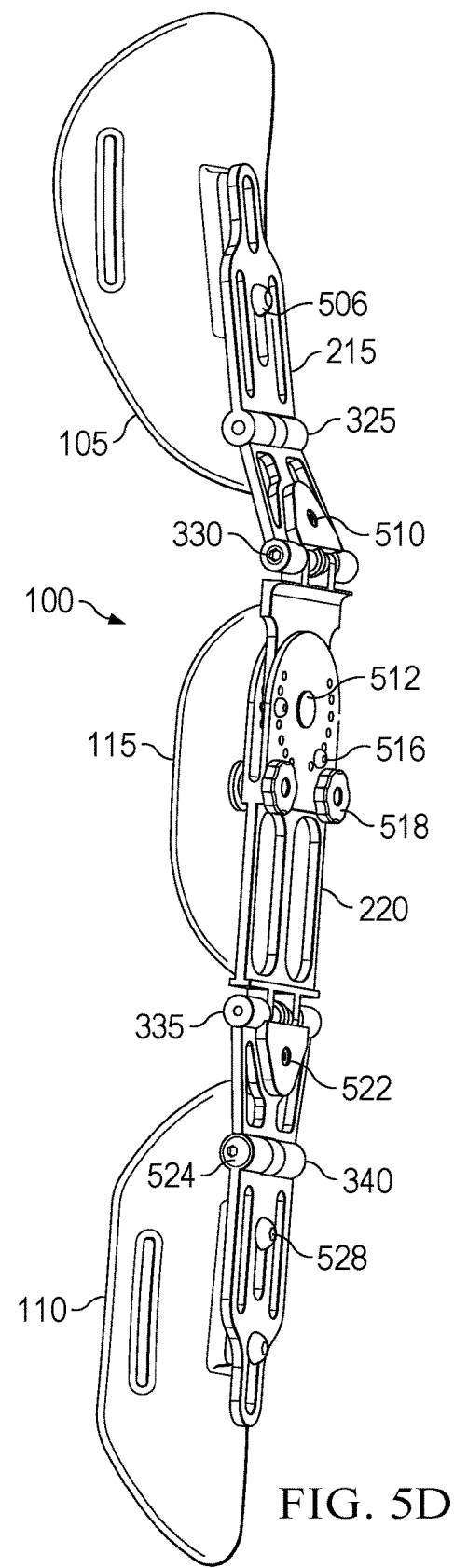

Turning to FIGS. 5A-5B, respective partial front views 500*a-b* are shown of an example adjustable, low-profile hip brace device to illustrate detailed views of some example features and mechanisms of one example implementation of the low-profile hip brace device. FIGS. 5C-5D provide corresponding partial side views 500*c-d* to show additional detailed views of the low-profile hip brace device 100. For instance, as shown in FIG. 5A, a section of an example hip brace device 100 is shown including the iliac crest pressure plate 105, the femur pressure plate 115, and a bracket segment 215 connecting the iliac crest pressure plate 105 to the femur pressure plate 115. As shown in this example, the iliac crest pressure plate 105, in some implementations, may include belt slots (e.g., 504), through which a strap may be fed to fasten a belt or other apparatus to the iliac crest pressure plate 105. For instance, in order to fasten the hip brace device 100 to a user, belts may be provided, for instance, to secure the hip brace (which has been adjusted to the contours of the user) to the waist and leg of the user. For instance, a waist belt device may be provided that includes a strap, which may be fed through the belt slots 504 to attach the belt to the hip brace 100 before attaching the belt (and hip brace) to a user. In other cases, slots 504 may be used to attach other elements to the hip brace 100, such as padding, ice packs (e.g., for cold therapy), among other examples. FIG. 5A further shows an example implementation of an adjustment mechanism 506 for the iliac crest plate 105. For instance, the bracket segment 215 may include lengthwise apertures, or openings, to serve as a track or guide in which a corresponding lockable bolt (e.g., an Allen bolt) positioned within the opening can slide to adjust the position of the iliac crest pressure plate 105 tracks on the bracket segment 215. When the iliac crest pressure plate 105 is positioned in the desired location, the bolt may be tightened to lock the plate 105 into position.

Continuing with the example of FIG. 5A, an adjustable locking hinge 325 is shown to enable adjustment of the angle of the iliac crest pressure plate 105 (to be provided in proximity to the user's Greater Trochanter). In this particular example, the hinge 325 may be implemented to be tightened and loosed by a locking teeth Allen bolt (e.g., 508) among other example implementations and features. A second hinge 330 may be provided, which is movable to adjust the hinge 330 (and thereby the femur plate 115) toward or away from the user's thigh (at or near the proximal femur of the patient). In some implementations, the hinge 330 may be implemented through a worm gear Allen adjustment. For instance, clockwise rotation of the Allen adjustment point 510 may cause the worm gear to adjust the hinge 330 (and the femur plate 115) towards the user's thigh, while counterclockwise rotation adjusts the hinge away from thigh. The angle of the femur pressure plate 115 may also be manipulated, such as introduced above. In the example of FIG. 5A, dials 518 may be provided through which one or both sides of the femur pressure plate 115 may be biased to the femur pressure plate 115 away from or toward the user (e.g., to create an anterior or posterior bias of the femur pressure plate 115).

When worn by and secured to a user, while in use, when the user's thigh flexes and extends relative to the hip, the femur and quadricep plates 115, 110 (and associated bracket segment 220) rotate smoothly about a pivot hinge 512 to facilitate the flexing and extending of the leg, while the iliac crest plate 105 remains positioned at the hip/waist. In some implementations, to customize and control the allowed range of motion of this pivot action (e.g., in connection with a physician-directed treatment plan), an example low-profile hip brace may additionally include a mechanism to adjust the allowed range of motion. For instance, a set of one or more openings may be provided in which motion stops (e.g., 516) may be inserted and secured to lock the range of motion stops for the brace 100. For instance, the openings may define a range of motion adjustable up to 90 degrees of flexion (or more) (e.g., range of motion restrictions ranging from −90 degrees extension to 90 degrees of flexion). In some instances, the motion stops may be implemented using thumb and finger screws (e.g., 516) or other rigid, securable elements to adjust the desired flexion/extension, among other example implementations. The opening(s) in which the screws or stops (e.g., 516) are inserted to define and customize the range of motion of the brace may, in some implementations, be implemented through multiple, discrete opening, each defining a respective, defined range of motion (e.g., as shown the example of FIGS. 5A-5D). In other implementations, the opening may be implemented as a single opening implementing a partial, circular track defining a continuous range of potential range of motion definitions, among other example implementations.

Continuing with the illustration of FIG. 5B, locking hinge 340, used to adjust the angle of quadricep plate 110, may be implemented in a manner analogous to locking hinge 325, for instance, with a locking teeth Allen bolt 524 utilized to fix the locking hinge 325 at a particular orientation. Additionally, hinge 335 may also be implemented as a worm gear hinge, with Allen adjustment point 522 utilized to adjust the hinge 335 inward (toward the user's leg) or outward (away from the user's leg) to thereby adjust the position of the femur pressure plate 115 relative to the quadricep pressure plate 110 (and iliac crest pressure plate 105). Counterpart quadricep plate adjustment mechanisms (e.g., implemented through openings and Allen bolts (e.g., 528) to allow the plate to slide up or down in the openings to a desired position and lock the quadricep plate 110 in that position). Further, strap slots (e.g., 526) may also be provided on the quadricep plate 110 (e.g., to allow a leg strap to be connected to the brace to connect the quadricep plate 110 to the leg of a user). FIGS. 5C and 5D show left- and right-side views of an example hip brace device 100 including the example features illustrated and discussed in connection with FIGS. 5A-5B.

Figure 6B:
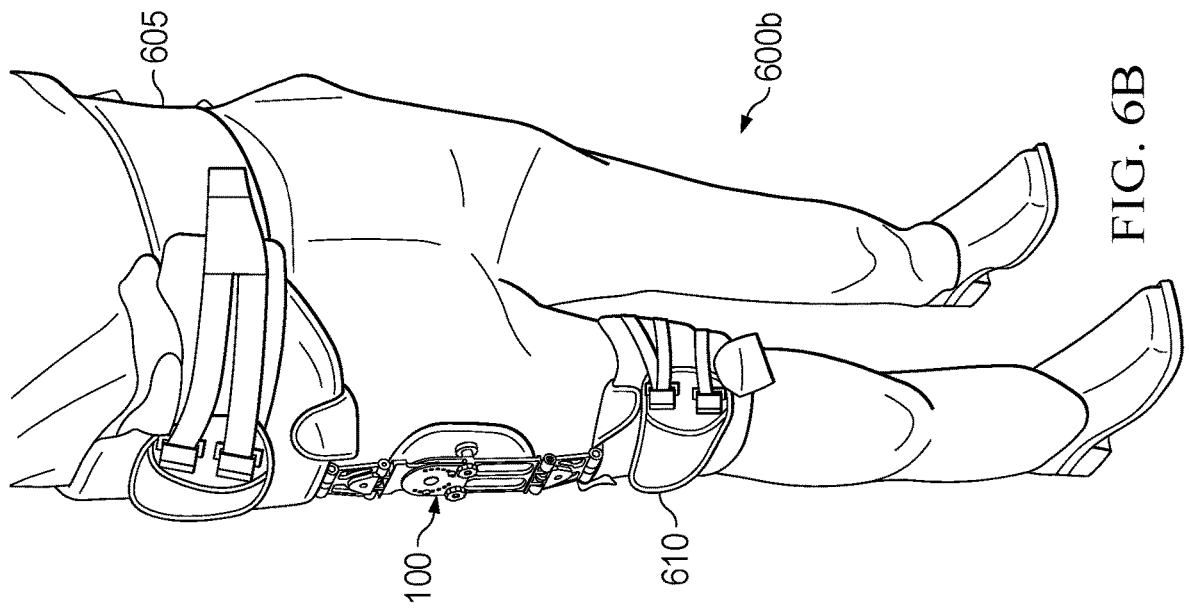
FIGS. 6A-6B are photographs of a user wearing an example adjustable, low-profile hip brace in accordance with at least some embodiments.
Figure 6A:
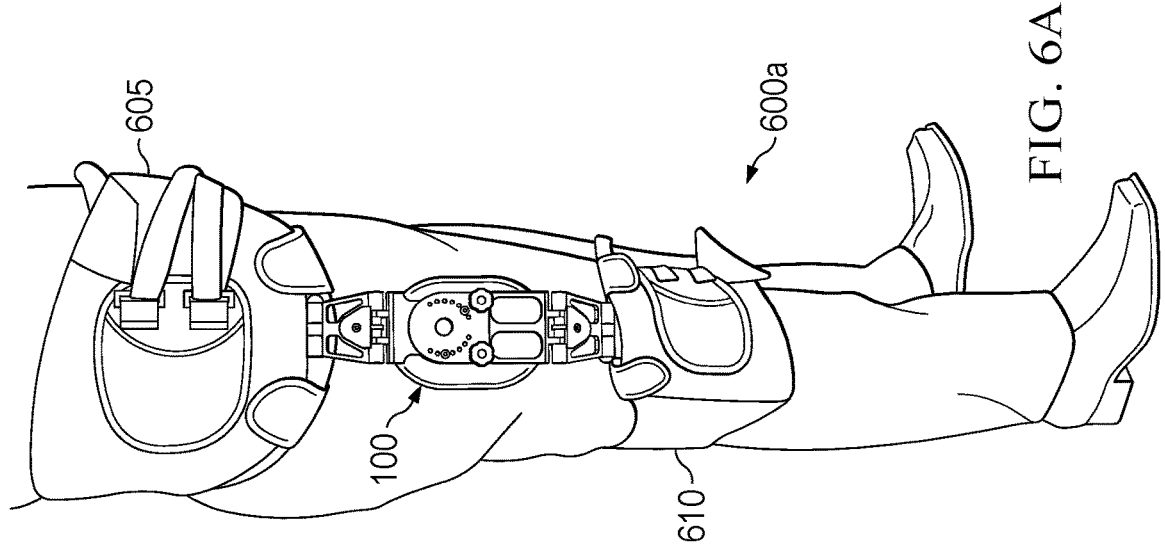

Turning to FIGS. 6A-6B, photographs 600*a-b* are shown illustrating an example low-profile adjustable hip brace device 100 worn by a human user. For instance, a waist or hip belt 605 may attach to the iliac crest pressure plate of the hip brace device and be used to secure the iliac crest pressure plate (e.g., after it has been adjusted to the proper position using the hip brace's multi-point adjustment mechanism at or near the hip of the user. Additionally, a thigh strap 610 may be provided to connect to the quadricep pressure plate to secure the quadricep at the distal thigh of the user and thus attach the hip brace to the user. In some implementations, one or both of the waist belt 605 and thigh belt 610 may be secured to the hip brace 100 using slots (e.g., corresponding strap slots on the iliac crest plate or quadricep plate) and a portion of the respective waist belt threaded through the slots. In other implementations, such as shown in the example of FIGS. 6A-6B, a waist belt 605 and/or thigh belt 610 may be implemented to include a pocket to receive the corresponding iliac crest or thigh plate and secure the plate to the belt (e.g., 605, 610).

Figure 7A:
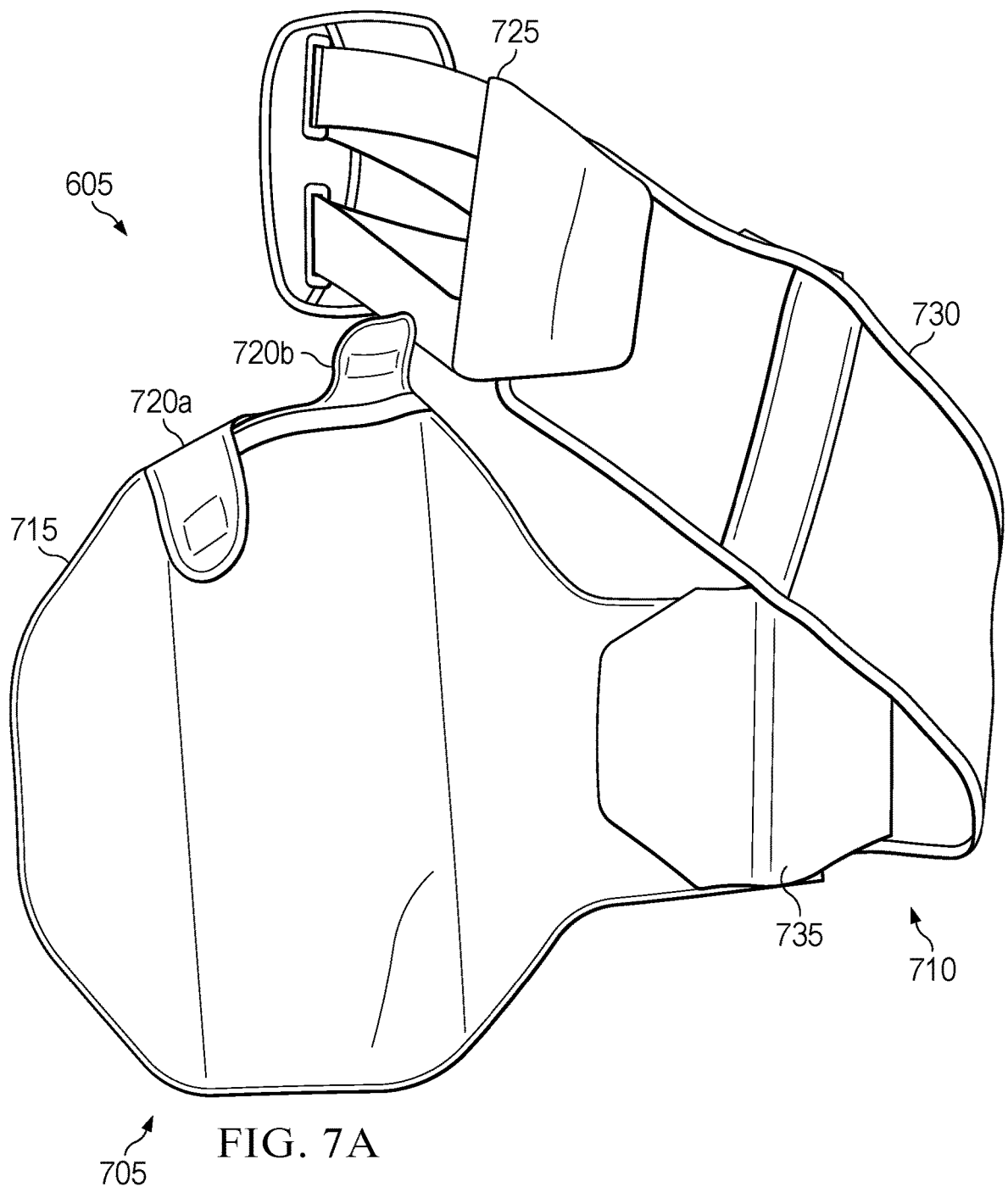
FIG. 7A is a view of an example waist belt to secure a hip brace to a user in accordance with at least some embodiments.

For instance, FIG. 7A illustrates a view of an example waist belt 605, such illustrated in the examples of FIGS. 6A-6B, in an open, unattached position (e.g., before it is connected to a hip brace and wrapped and secured around a user's waist). In one example implementation, belts used to secure a hip brace to a user may themselves be multi-point-adjustable and composed of multiple segments. For instance, the belt 605 shown in FIG. 7A may be composed of segments such as an iliac crest plate strap segment 705, an extension strap segment 710, and an A-frame tab segment 725. The plate strap segment 705 may include a pocket section 715, which may receive at least a portion of the iliac crest pressure plate of a hip brace device and tabs (e.g., 720a, 720b), which may be used to secure the iliac crest pressure plate within the pocket 715 (e.g., through snaps, hook-and-loop (e.g., Velcro™), buttons, or other attachment mechanism). The extension strap segment 710 may include an extension strap 730, which may be attached to the A-frame tab segment 725 (e.g., using two or more hook-and-loop (or other attachment) mechanisms on the A-frame tab segment 725) on one end of the extension strap 730 and attached to the plate strap segment 705 on the other end of the extension strap 730 through an attachment mechanism, such as an alligator attachment tab 735.

Figure 7B:
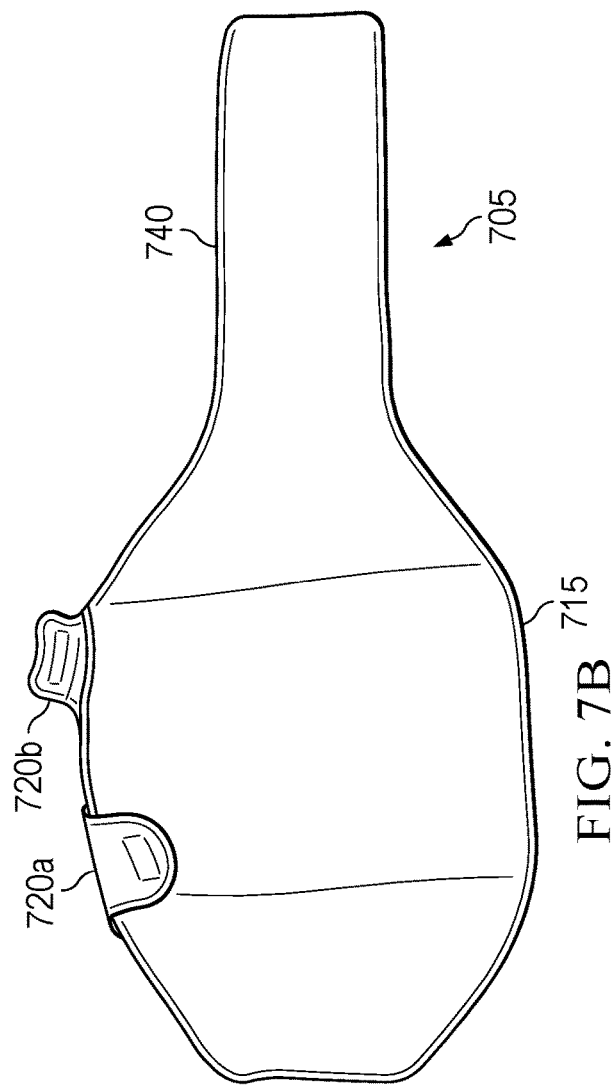
FIGS. 7B-7F are views of segments of an example waist belt in accordance with at least some embodiments.
Figure 8A:
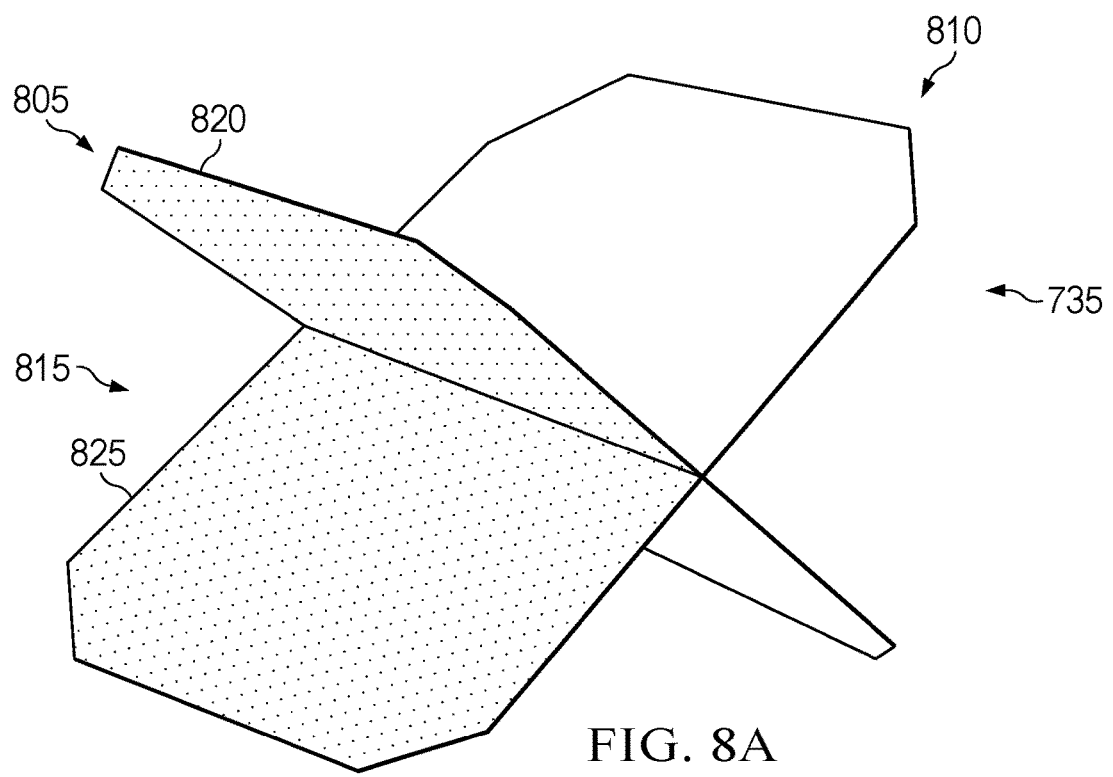
FIGS. 8A-8C are views of an example alligator attachment tab in accordance with at least some embodiments.
Figure 8B:
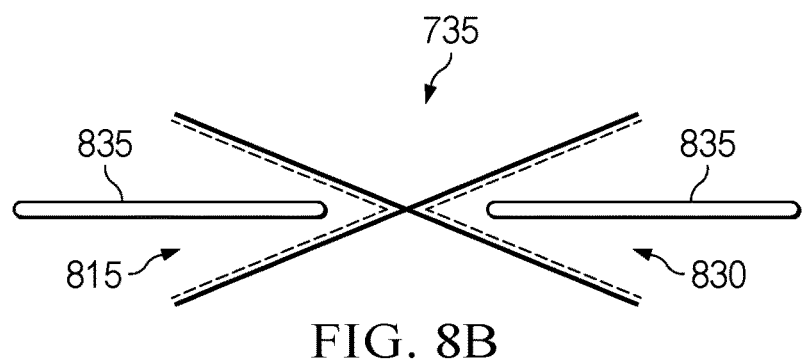
Figure 8C:
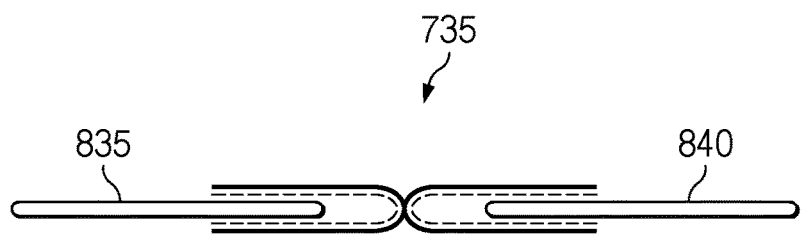

Turning to FIG. 7B, an isolated view of the plate strap segment 705 is shown. In addition to a plate pocket 715 and mechanisms to secure a pressure plate of a hip brace in the pocket 715 (e.g., hook-and-loop tabs 720a, b), an example plate strap segment 705 may additionally include an extension section 740, which may be trimmed (e.g., along with the extension strap 730) to adjust the overall length of the assembled waist belt 605 to the waist measurements for a particular patient/user. The plate strap segment 705 may be connected to the extension strap by an alligator attachment tab at an end (e.g., trimmed end) of the extension section of the plate strap segment. An example alligator attachment tab 735 is illustrated in FIGS. 8A-8C. An example alligator tab 735 may have one or both sides (e.g., 805, 810), which embody an alligator clamp-style tab, where the "mouth" 815 of the tab includes is lined with either the hooks or loops of a hook-and-loop-type fastener to correspond to the material the alligator tab's mouth is to fasten to. In some implementations, the bottom (e.g., 820) and roof (e.g., 825) of the tab mouth 815 may be lined with the same type of hook-and-loop material, while in other instances, the bottom 820 of the mouth 815 is lined with one of the hook-and-loop materials (e.g., hooks), while the bottom of the mouth 815 is lined with the other. Further, while some alligator attachment tabs may only include one mouth (e.g., at one side 805) of the tab (e.g., 735), in other instances (such as illustrated in FIGS. 8A-8C), both sides 805, 810 may each include a mouth (e.g., 815, 830) to clamp on (through applied external pressure) and fasten on another material. For instance, as shown in FIGS. 8B-8C, a material (e.g., 835, 840) may be inserted within the mouth(s) (e.g., 815, 830) of an example alligator attachment tab (as shown in FIG. 8B) and the roof and bottom of the mouth may be attached, via a respective hook-and-loop connection with material on complimentary sides of the material (e.g., 835, 840), to clamp the alligator attachment tab to the material, such as illustrated in FIG. 8C. Through the use of an alligator attachment tab (e.g., 735), two materials or segments (e.g., 835, 840) of an apparatus may be (removably) joined together.

Figure 7C:
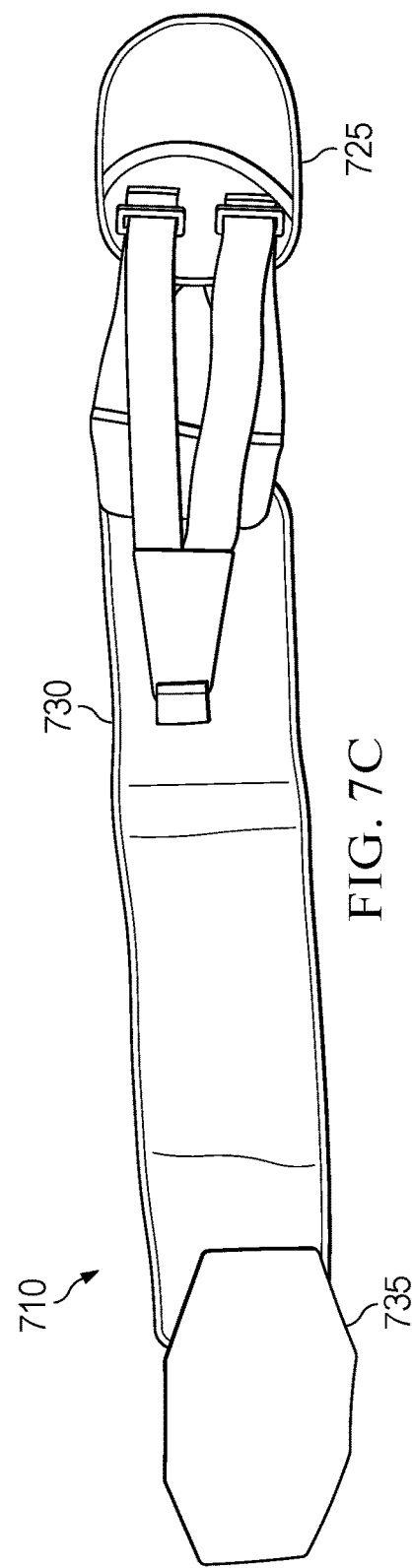
Figure 7D:
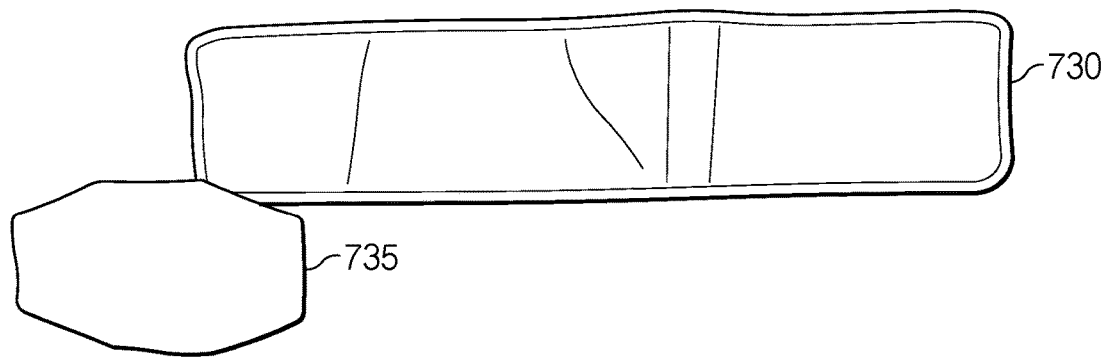
Figure 7E:
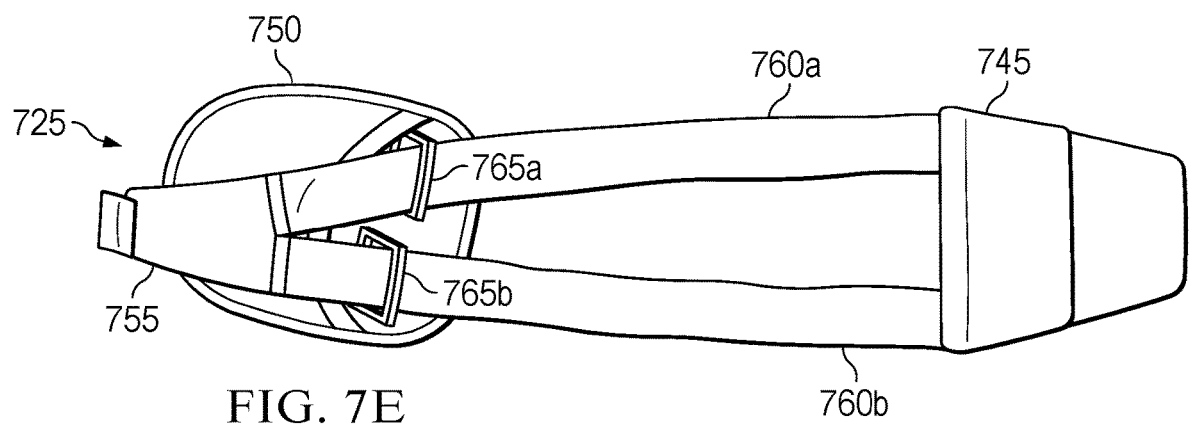
Figure 7F:
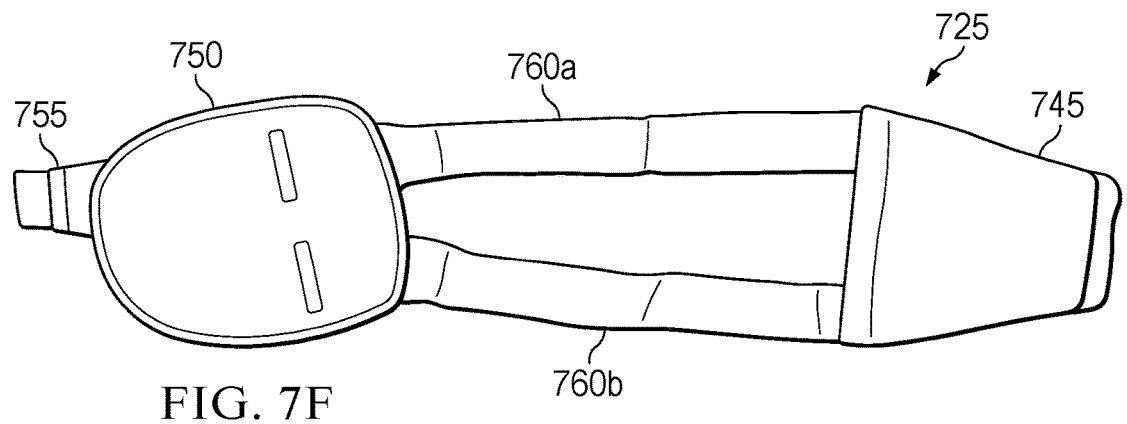

Turning to FIG. 7C, an isolated view of an example extension strap segment 710 of a waist belt apparatus is shown. The body 730 of the extension strap 710 may be trimmed to adapt the strap to the dimensions of a particular user. Respective alligator attachment tabs (e.g., 735 and 745 (integrated with A-frame tab segment 725) may be connected to the (appropriately trimmed) extension strap. As noted above alligator attachment tab 735 may be used to connect the extension strap segment 710 to the plate strap segment (e.g., 705). As shown in FIG. 7D, the extension strap segment 710 may include an extension strap 730 and an alligator attachment tab 735 (show detached from the extension strap 730). FIGS. 7E-7F show front and back views of the a-frame tab segment 725. The A-frame tab segment 725 may include three hook-and-loop-like surfaces. For instance, A-frame straps 760a, b may pass through respective belt closure D-rings 765a, b, the A-frame straps connecting a (one-sided) alligator attachment tab 745 integrally connected (at the non-alligator end of the tab 745) to the A-frame straps 760a, b to a relatively narrower A-frame hook-and-loop tab 755. The alligator attachment tab 745 of the A-frame tab segment 725 is configured to attach to an end of the extension strap 730 (the end opposite the end connected to the iliac crest pressure plate pad segment). A front view of the A-frame tab segment (shown in FIG. 7E) shows the presence of hook-and-loop-material on the front surface of A-frame tab 755. The back view of the A-frame tab segment shows the presence of hook-and-loop-material on the back-side surface of belt closure tab 750. The hook-and-loop material of the A-frame tab segment 755 is configured to attach to a surface of the iliac crest pressure plate pad when the waist belt apparatus is assembled. The assembled waist belt device may be wrapped around the waist of the user and the hook-and-loop surface of the belt closure tab 750 is brought into contact with a surface of the iliac crest plate strap segment 705 (e.g., on or near the pocket portion of the iliac crest plate strap segment 705). The waist belt may be strapped onto the user before or after the iliac crest pressure plate of the hip brace is inserted into the iliac crest plate strap segment 705 pocket. The A-frame strap tab segment 725 may be used to tighten the belt snugly around the user's waste, by pulling the A-frame hook-and-loop tab to extend the A-frame straps further through the D-rings of the A-frame strap tab segment 725 and fastening the (hook-and-loop side of the) A-frame hook-and-loop tab to an exposed surface of the extension strap (e.g., 730).

Figure 9A:
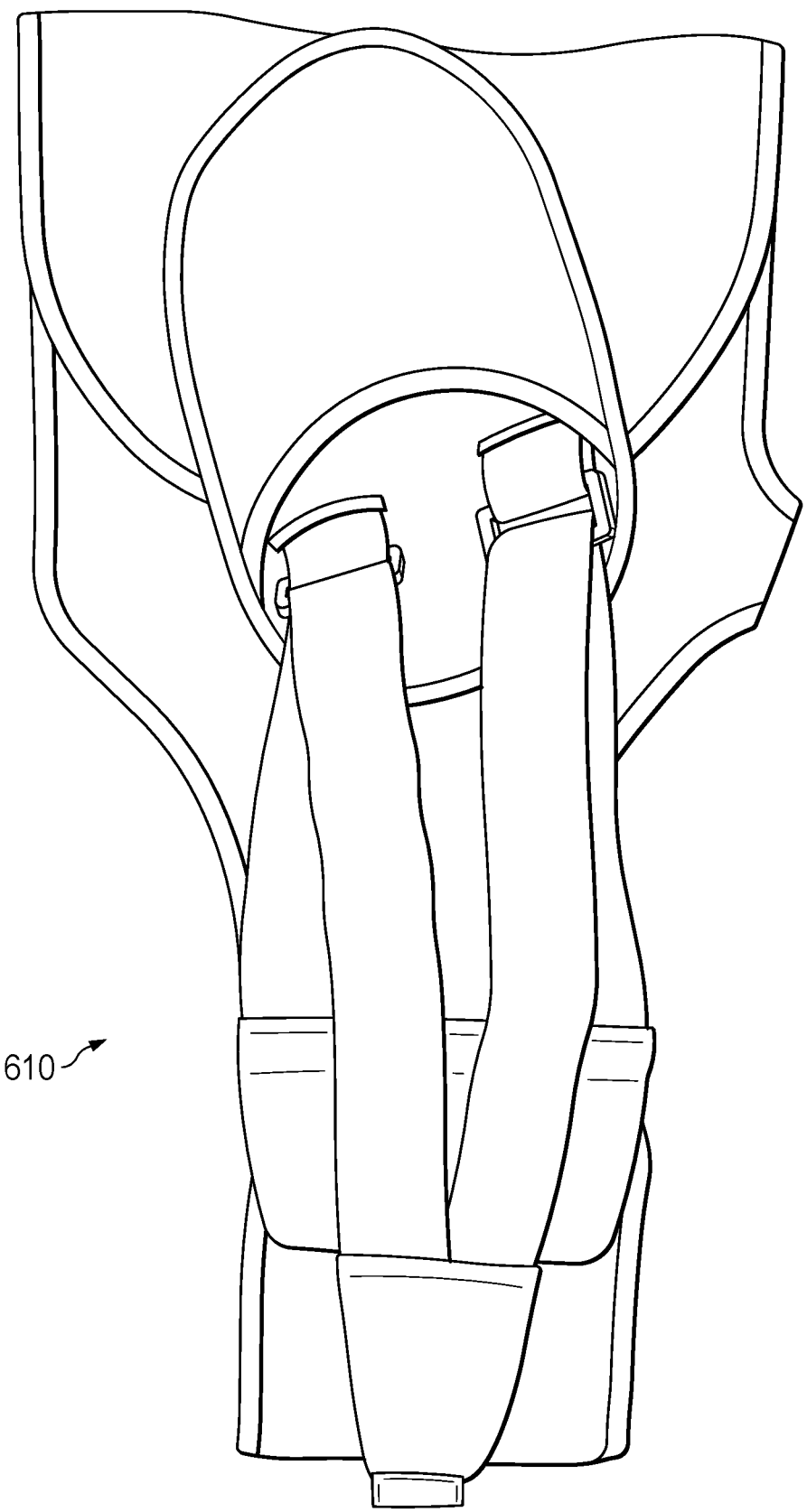
FIG. 9A is a view of an example thigh belt to secure a hip brace to a user in accordance with at least some embodiments
Figure 9B:
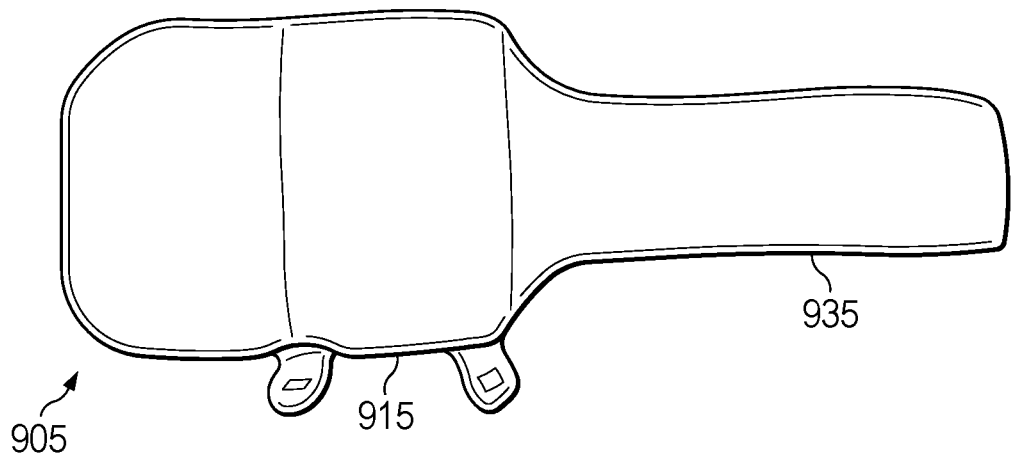
FIGS. 9B-9D are views of segments of an example thigh belt in accordance with at least some embodiments.
Figure 9C:
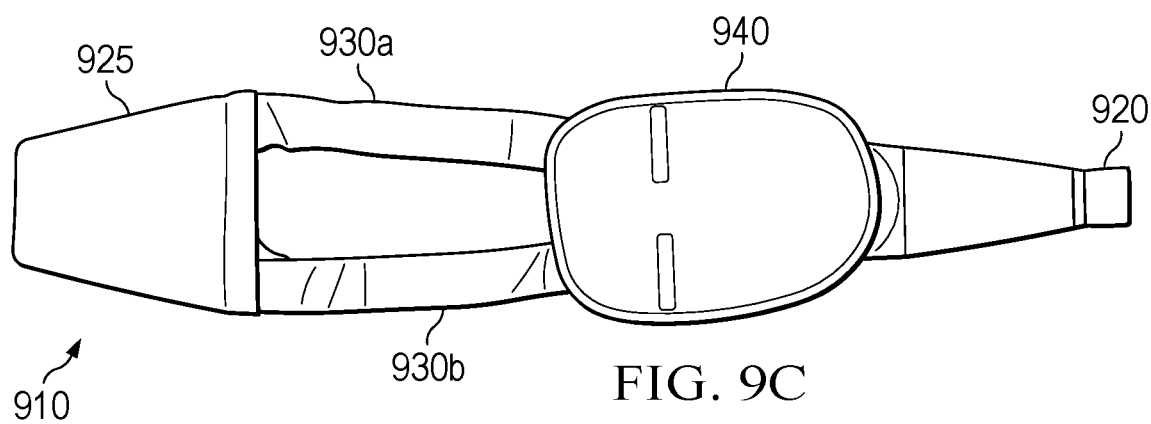
Figure 9D:
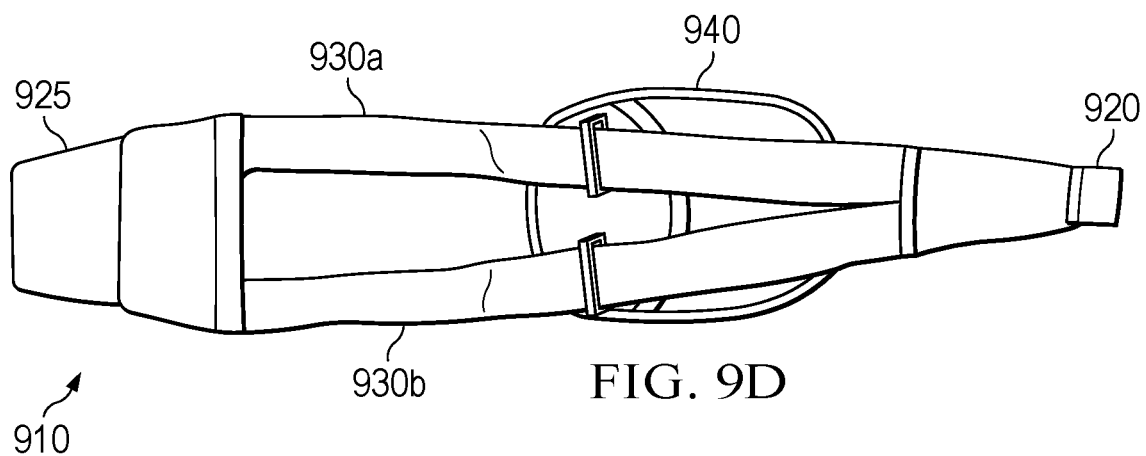

The principles employed in the example waist belt device may also be applied equally to thigh belt devices. For instance, FIGS. 9A-9D illustrate views of an example thigh belt device and its subcomponents. For instance, FIG. 9A shows a view of an example thigh belt 610 in a closed position (e.g., associated with the thigh belt 610 being wrapped around the leg of a user). As with the example waist belt discussed in the examples above, a thigh belt for an example hip brace may be detachably assembled from multiple belt segments to customize the size of the belt to multiple different users (e.g., different leg sizes). For instance, as shown in FIGS. 9B-9D, an example thigh belt 610 may be assembled by attaching a quadricep strap segment 905 to an A-frame tab segment 910. In this example, the segments of a thigh belt 610 are similar to those discussed in connection with the example waist belt with the omission of an extra extension strap segment present in the example waist belt. Indeed, it should be appreciated that some of the segments may be reused in both waist belts and thigh belts. While the quadricep strap segment 905 may include a pocket (e.g., 915) that is configured to accept a quadricep pressure plate (which may be different in dimensions from an iliac crest pressure plate to be accepted by the iliac crest plate strap segment), the A-frame tab segment 910 of the thigh belt may include the same or similar components as that of the A-frame tab segment of a waist belt (e.g., an A-frame hook-and-loop tab 920 connected to a one-sided alligator attachment tab 925 by two A-frame straps 930*a,b*). In this example, an alligator attachment tab 925 on the A-frame tab segment 910 may be used to couple the A-frame tab segment 910 to an extension portion 935 of the quadricep strap segment 905. The extension portion 935 may be trimmed (e.g., prior to assemble) to meet the dimensions of the intended patient/user's leg (e.g., the leg circumference). The A-frame tab segment 910 may also include a thigh belt closure pad 940 with hook-and-loop material on one side to attach to a surface of the quadricep strap segment 905. Attaching the thigh belt closure pad 940 to the quadricep strap segment 905 may be the first step in securing the thigh belt to a user, with the A-frame hook-and-loop tab's 920 attachment to the extension portion 935 serving to further tighten and secure the fit of the thigh belt (and quadricep pressure plate) to the patient/user.

FIGS. 10A-10B illustrate the placement of a pressure plate (e.g., iliac crest pressure plate 105) within the pocket (e.g., 715) of an example belt utilized to secure a hip brace device (such as an adjustable, low-profile hip brace device as discussed herein) to a user. As shown in FIG. 10A, a pressure plate (e.g., an iliac crest pressure plate or quadricep pressure plate) may be inserted into an opening 1005 of the pocket portion of an example belt. When the plate (e.g., 105) is fully positioned within the pocket (e.g., 715), the plate may be secured within the pocket, for instance, by engaging fasteners provided on the belt. For instance, as shown in the example of FIG. 10B, with the plate (e.g., iliac crest pressure plate) positioned fully within the pocket of the belt, tabs 720*a, b* may be folded over the edge of the pressure plates and fastened to the other side of the pocket. For instance, fastener tabs (e.g., 720*a, b*) may be provided with hook-and-loop fasteners to fasten to the surface of the pocket portion of the belt and secure the belt (e.g., a waist belt or thigh belt) to the hip brace (e.g., at the iliac crest pressure plate or quadricep pressure plate). Other plates (e.g., a femur pressure plate 115) may be left uncovered and may be unconnected to the belts (e.g., waist belt and thigh belt) used to attach the hip brace to the user, among other example implementations.

Further, portions of a belt utilized to connect the hip brace to a user (or portions of the hip brace itself (e.g., the component pressure plates)) may also include pockets or other attachment mechanisms to attach warm or cold therapy pads or packs for application at the joint(s) of the user, while the hip brace is worn. For instance, a packet portion of a waist belt or the iliac crest pressure plate may include a pocket configured to accept cold therapy pads to efficiently apply cold therapy near the site of contact and protect the user's skin from cold damage due to a built-in barrier provided by the pocket between the cold therapy pack and the skin. Other features may likewise be added and employed making use of the structure of the hip brace device and/or belts utilized to secure the hip brace to a user, among other example features and embodiments.

Reference throughout this specification to "one implementation," "an implementation," "an example implementation," "an example," "one example, "an instance", or "one instance" means that a particular feature, structure, or characteristic described in connection with the implementation is included in at least one implementation of the present invention. Thus, the appearances of the phrases "in one implementation" or "in an implementation" in various places throughout this specification are not necessarily all referring to the same implementation. Furthermore, the particular features, structures, or characteristics may be combined in any suitable manner in one or more implementations.

The following examples pertain to embodiments in accordance with this Specification. Example 1 is an adjustable hip brace to prevent adduction and abduction of a hip of a user, where the hip brace includes: an iliac crest pressure plate; a femur pressure plate; a quadriceps pressure plate; and a bracket including one or more adjustable hinges to adjust positioning of at least one of the iliac crest pressure plate, the femur pressure plate, or the quadriceps pressure plate to correspond with dimensions of the user, and the bracket further includes a range of motion restriction dial to control flexion and/or extension of the hip of the user, where the iliac crest pressure plate, the femur pressure plate, and the quadriceps pressure plate are each attached to the bracket, and the range of motion restriction is positioned on the bracket to correspond to the femur pressure plate.

Example 2 includes the subject matter of example 1, where the one or more adjustable hinges includes one or more locking hinges.

Example 3 includes the subject matter of example 2, where the one or more locking hinges include an upper locking hinge positioned between the iliac crest pressure plate and femur pressure plate, where the upper locking hinge is configurable to adjust position of the iliac crest pressure plate.

Example 4 includes the subject matter of example 3, where the iliac crest pressure plate is to be adjusted to dimensions of a waist of the user.

Example 5 includes the subject matter of any one of examples 2-4, where the one or more locking hinges includes a lower locking hinge positioned between the femur pressure plate and the quadriceps pressure plate, where the lower locking hinge is configurable to adjust position of the quadriceps pressure plate.

Example 6 includes the subject matter of example 5, where the quadriceps pressure plate is to be adjusted to dimensions of a thigh of the user.

Example 7 includes the subject matter of any one of examples 2-6, where the one or more locking hinges include locking hinges adjustable with a locking teeth bolt.

Example 8 includes the subject matter of any one of examples 1-7, where the one or more adjustable hinges include one or more worm gear hinges configurable to adjust position of the femur pressure plate.

Example 9 includes the subject matter of example 8, where the one or more worm gear hinges include an upper worm gear hinge positioned between the iliac crest pressure plate and the femur pressure plate.

Example 10 includes the subject matter of any one of examples 8-9, where the one or more worm gear hinges include a lower worm gear hinge positioned between the quadriceps pressure plate and the femur pressure plate.

Example 11 includes the subject matter of any one of examples 1-10, where the one or more adjustable hinges includes a particular hinge to adjust anterior and posterior bias of the femur plate on a thigh of the user.

Example 12 includes the subject matter of example 11, where the particular hinge is adjustable through a posterior bias dial and an anterior bias dial.

Example 13 includes the subject matter of any one of examples 11-12, where the particular hinge is to further adjust an amount of pressure applied to the thigh at the femur plate.

Example 14 includes the subject matter of any one of examples 1-13, further including one or more sliding lock bolts to slidably adjust an overall length of the hip brace.

Example 15 includes the subject matter of example 14, where each of the one or more sliding lock bolts include a respective bolt and opening, where the bolt slides within the opening to adjust the length of the hip brace, and the sliding lock bolts connect the bracket to one or more of the iliac crest pressure plate and the quadriceps pressure plate.

Example 16 includes the subject matter of example 15, where the bolt of each sliding lock bolt is connected to one of the pressure plates and the corresponding opening is provided in the bracket.

Example 17 includes the subject matter of any one of examples 15-16, where each sliding lock bolt includes two or more bolts to slide within two or more corresponding openings.

Example 18 includes the subject matter of any one of examples 1-17, where one or more of the iliac crest pressure plate, the femur pressure plate, or the quadriceps pressure plate includes a rigid contoured plate and padding attached to the rigid contoured plate.

Example 19 includes the subject matter of any one of examples 1-18, where the range of motion restriction dial defines a plurality of available ranges of motion, flexion and/or extension of the hip is restricted according to a selected one of the available ranges of motion, and the range of motion restriction dial includes one or more locks to lock the range of motion restriction dial to select one of the available ranges of motion.

Example 20 includes the subject matter of any one of examples 1-19, where the range of motion restriction dial includes a substantially circular track opening and one or more elements to move within the circular track opening to support a limited range of flexion and/or extension of the hip.

Example 21 includes the subject matter of any one of examples 1-20, further including an upper strap to connect to iliac crest pressure plate and wrap around a waist of the user and a lower strap to connect to the quadriceps pressure plate and wrap around a leg of the user, where the upper and lower straps secure the hip brace to the user.

Example 22 includes the subject matter of example 21, where one or more of the upper strap or the lower strap include a respective pocket to receive and connect to a corresponding one of the iliac crest pressure plate or the quadriceps pressure plate.

Example 23 includes the subject matter of example 21, where one or more of the iliac crest pressure plate or the quadriceps pressure plate include a slot through which a corresponding one of the upper strap or the lower strap is to connect to the corresponding pressure plate.

Example 24 includes the subject matter of any one of examples 21-23, where the one or more of the upper strap or the lower strap include an A-frame strap.

Example 25 includes the subject matter of any one of examples 1-24, further including attachments at one or more of the iliac crest pressure plate, the femur pressure plate, or the quadriceps pressure plate to attach a cold therapy device to the corresponding plate.

Example 26 is a method for using the hip brace of any one of examples 1-25 to provide a treatment associated with the hip of the user.

Example 27 includes the subject matter of example 26, where the treatment includes a post-operative rehabilitation treatment.

Example 28 includes the subject matter of any one of examples 26-27, where the treatment includes a cold treatment.

Example 29 includes the subject matter of any one of examples 26-28, where the treatment includes a bracing of the hip of the user.

Example 30 includes the subject matter of any one of examples 26-29, further including adjusting one or more of the hinges of the hip brace to customize dimensions of the hip brace to the user.

Example 31 is an apparatus including a hip brace including: an iliac crest pressure plate; a femur pressure plate; a quadriceps pressure plate; and a bracket including one or more adjustable hinges to adjust positioning of at least one of the iliac crest pressure plate, the femur pressure plate, or the quadriceps pressure plate to correspond with dimensions of the user, and the bracket further includes a range of motion restriction dial to control flexion or extension of the hip of the user, where the iliac crest pressure plate, the femur pressure plate, and the quadriceps pressure plate are each attached to the bracket, and the range of motion restriction is positioned on the bracket to correspond to the femur pressure plate, where the one or more adjustable hinges include: an upper locking hinge positioned between the iliac crest pressure plate and femur pressure plate, where the upper locking hinge is configurable to adjust an angle of the iliac crest pressure plate; a lower locking hinge positioned between the femur pressure plate and the quadriceps pressure plate, where the lower locking hinge is configurable to adjust an angle of the quadriceps pressure plate; an upper worm gear hinge positioned between the iliac crest pressure plate and the femur pressure plate; a lower worm gear hinge positioned between the quadriceps pressure plate and the femur pressure plate; and a particular hinge to adjust anterior and posterior bias of the femur plate on a thigh of the user; where the bracket further includes: an upper sliding lock bolt to slidably adjust position of the iliac crest pressure plate; and a lower slide lock bolt to slidably adjust position of the quadriceps pressure plate.

Example 32 is a method for using a hip brace to provide a treatment associated with the hip of the user, where the method includes: attaching the hip brace to the body of the user using one or more straps connected to the hip brace, where the hip brace includes: an iliac crest pressure plate; a femur pressure plate; a quadriceps pressure plate; and a bracket comprising one or more adjustable hinges to adjust positioning of at least one of the iliac crest pressure plate, the femur pressure plate, or the quadriceps pressure plate to correspond with dimensions of the user, and the bracket further includes a range of motion restriction dial to control flexion or extension of the hip of the user, where the iliac crest pressure plate, the femur pressure plate, and the quadriceps pressure plate are each attached to the bracket, and the range of motion restriction is positioned on the bracket to correspond to the femur pressure plate.

Thus, particular embodiments of the subject matter have been described. Other embodiments are within the scope of the following claims. In some cases, the actions recited in the claims can be performed in a different order and still achieve desirable results. In addition, the processes depicted in the accompanying figures do not necessarily require the particular order shown, or sequential order, to achieve desirable results.

A detailed description has been given with reference to specific exemplary embodiments. It will, however, be evident that various modifications and changes may be made thereto without departing from the broader spirit and scope of the invention as set forth in the appended claims. The specification and drawings are, accordingly, to be regarded in an illustrative sense rather than a restrictive sense. Furthermore, the foregoing use of embodiment and other exemplarily language does not necessarily refer to the same embodiment or the same example, but may refer to different and distinct embodiments, as well as potentially the same embodiment.

The invention claimed is:

1. An adjustable hip brace to prevent adduction and abduction of a hip of a user, wherein the hip brace comprises:
    an iliac crest pressure plate;
    a femur pressure plate;
    a quadriceps pressure plate; and
    a bracket comprising one or more adjustable hinges to adjust positioning of at least one of the iliac crest pressure plate, the femur pressure plate, or the quadriceps pressure plate to correspond with dimensions of the user, and the bracket further comprises a range of motion restriction dial to control flexion or extension of the hip of the user,
    wherein the iliac crest pressure plate, the femur pressure plate, and the quadriceps pressure plate are each attached to the bracket, and the range of motion restriction dial is positioned on the bracket to correspond to the femur pressure plate.

2. The hip brace of claim 1, wherein the one or more adjustable hinges comprises one or more locking hinges.

3. The hip brace of claim 2, wherein the one or more locking hinges comprise an upper locking hinge positioned between the iliac crest pressure plate and femur pressure plate, wherein the upper locking hinge is configurable to adjust position of the iliac crest pressure plate.

4. The hip brace of claim 3, wherein the iliac crest pressure plate is to be adjusted to dimensions of a waist of the user.

5. The hip brace of claim 2, wherein the one or more locking hinges comprises a lower locking hinge positioned between the femur pressure plate and the quadriceps pressure plate, wherein the lower locking hinge is configurable to adjust position of the quadriceps pressure plate.

6. The hip brace of claim 5, wherein the quadriceps pressure plate is to be adjusted to dimensions of a thigh of the user.

7. The hip brace of claim 2, wherein the one or more locking hinges comprise locking hinges adjustable with a locking teeth bolt.

8. The hip brace of claim 1, wherein the one or more adjustable hinges comprise one or more worm gear hinges configurable to adjust position of the femur pressure plate.

9. The hip brace of claim 8, wherein the one or more worm gear hinges comprise an upper worm gear hinge positioned between the iliac crest pressure plate and the femur pressure plate.

10. The hip brace of claim 8, wherein the one or more worm gear hinges comprise a lower worm gear hinge positioned between the quadriceps pressure plate and the femur pressure plate.

11. The hip brace of claim 1, wherein the one or more adjustable hinges comprises a particular hinge to adjust anterior and posterior bias of the femur plate on a thigh of the user.

12. The hip brace of claim 11, wherein the particular hinge is adjustable through a posterior bias dial and an anterior bias dial.

13. The hip brace of claim 11, wherein the particular hinge is to further adjust an amount of pressure applied to the thigh at the femur plate.

14. The hip brace of claim 1, further comprising one or more sliding lock bolts to slidably adjust an overall length of the hip brace.

15. The hip brace of claim 14, wherein each of the one or more sliding lock bolts comprise a respective bolt and opening, wherein the bolt slides within the opening to adjust the length of the hip brace, and the sliding lock bolts connect the bracket to one or more of the iliac crest pressure plate and the quadriceps pressure plate.

16. The hip brace of claim 15, wherein the bolt of each sliding lock bolt is connected to one of the pressure plates and the corresponding opening is provided in the bracket.

17. The hip brace of claim 15, wherein each sliding lock bolt comprises two or more bolts to slide within two or more corresponding openings.

18. The hip brace of claim 1, wherein one or more of the iliac crest pressure plate, the femur pressure plate, or the quadriceps pressure plate comprises a rigid contoured plate and padding attached to the rigid contoured plate.

19. The hip brace of claim 1, wherein the range of motion restriction dial defines a plurality of available ranges of motion, flexion or extension of the hip is restricted according to a selected one of the available ranges of motion, and the range of motion restriction dial comprises one or more locks to lock the range of motion restriction dial to select one of the available ranges of motion.

20. The hip brace of claim 1, wherein the range of motion restriction dial comprises a substantially circular track opening and one or more elements configured to repositioned within the circular track opening to define one of a continuous set of range of motion options for the hip brace and define range of flexion or extension of the hip.

21. A method for using a hip brace to provide a treatment associated with the hip of a user, wherein the method comprises:
    attaching the hip brace to the body of the user using one or more straps connected to the hip brace, wherein the hip brace comprises:
    an iliac crest pressure plate;
    a femur pressure plate;
    a quadriceps pressure plate; and
    a bracket comprising one or more adjustable hinges to adjust positioning of at least one of the iliac crest pressure plate, the femur pressure plate, or the quadriceps pressure plate to correspond with dimensions of the user, and the bracket further comprises a range of motion restriction dial to control flexion or extension of the hip of the user,
    wherein the iliac crest pressure plate, the femur pressure plate, and the quadriceps pressure plate are each attached to the bracket, and the range of motion restriction dial is positioned on the bracket to correspond to the femur pressure plate.

22. The method of claim 21, wherein the treatment comprises a post-operative rehabilitation treatment.

23. The method of claim 21, wherein the treatment comprises a cold treatment.

24. The method of claim 21, wherein the treatment comprises a bracing of the hip of the user.

25. The method of claim 21, further comprising adjusting one or more of the hinges of the hip brace to customize dimensions of the hip brace to the user.

26. An apparatus comprising a hip brace comprising:
an iliac crest pressure plate;
a femur pressure plate;
a quadriceps pressure plate; and
a bracket comprising one or more adjustable hinges to adjust positioning of at least one of the iliac crest pressure plate, the femur pressure plate, or the quadriceps pressure plate to correspond with dimensions of a user, and the bracket further comprises a range of motion restriction dial to control flexion or extension of the hip of the user,
wherein the iliac crest pressure plate, the femur pressure plate, and the quadriceps pressure plate are each attached to the bracket, and the range of motion restriction dial is positioned on the bracket to correspond to the femur pressure plate,
wherein the one or more adjustable hinges comprise:
an upper locking hinge positioned between the iliac crest pressure plate and femur pressure plate, wherein the upper locking hinge is configurable to adjust an angle of the iliac crest pressure plate;
a lower locking hinge positioned between the femur pressure plate and the quadriceps pressure plate, wherein the lower locking hinge is configurable to adjust an angle of the quadriceps pressure plate;
an upper worm gear hinge positioned between the iliac crest pressure plate and the femur pressure plate;
a lower worm gear hinge positioned between the quadriceps pressure plate and the femur pressure plate; and
a particular hinge to adjust anterior and posterior bias of the femur plate on a thigh of the user;
wherein the bracket further comprises:
an upper sliding lock bolt to slidably adjust position of the iliac crest pressure plate; and
a lower slide lock bolt to slidably adjust position of the quadriceps pressure plate.

* * * * *